(12) United States Patent
Derchak et al.

(10) Patent No.: US 8,177,724 B2
(45) Date of Patent: May 15, 2012

(54) SYSTEM AND METHOD FOR SNORE DETECTION AND CONFIRMATION

(75) Inventors: P. Alexander Derchak, Summit, NJ (US); Lance Myers, Ventura, CA (US); Gary Michael Lucia, Ventura, CA (US)

(73) Assignee: adidas AG, Herzogenaurach (DE)

( * ) Notice: Subject to any disclaimer, the term of this patent is extended or adjusted under 35 U.S.C. 154(b) by 1306 days.

(21) Appl. No.: 11/758,581

(22) Filed: Jun. 5, 2007

(65) Prior Publication Data

US 2007/0287896 A1    Dec. 13, 2007

Related U.S. Application Data

(60) Provisional application No. 60/811,777, filed on Jun. 8, 2006.

(51) Int. Cl.
*A61B 5/08* (2006.01)
(52) U.S. Cl. .......... 600/529; 600/532; 600/538
(58) Field of Classification Search .......... 600/529–543
See application file for complete search history.

(56) References Cited

U.S. PATENT DOCUMENTS

| | | | |
|---|---|---|---|
| 4,016,868 A | 4/1977 | Allison | 600/388 |
| 4,308,872 A | 1/1982 | Watson et al. | 600/538 |
| 4,373,534 A | 2/1983 | Watson | 600/538 |
| 4,433,693 A | 2/1984 | Hochstein | 600/534 |
| 4,452,252 A | 6/1984 | Sackner | 600/484 |
| 4,456,015 A | 6/1984 | Sackner | 600/534 |
| 4,648,407 A | 3/1987 | Sackner | 600/534 |
| 4,753,088 A | 6/1988 | Harrison et al. | |
| 4,753,988 A | 6/1988 | Henton et al. | 525/73 |
| 4,777,962 A | 10/1988 | Watson et al. | 600/529 |
| 4,800,495 A | 1/1989 | Smith | 600/322 |
| 4,807,640 A | 2/1989 | Watson et al. | 600/534 |
| 4,815,473 A | 3/1989 | Watson et al. | 600/534 |
| 4,817,625 A | 4/1989 | Miles | 600/534 |
| 4,834,109 A | 5/1989 | Watson | 600/534 |
| 4,860,766 A | 8/1989 | Sackner | 600/561 |
| 4,960,118 A | 10/1990 | Pennock | 128/200.24 |
| 4,966,155 A | 10/1990 | Jackson | 600/484 |
| 4,986,277 A | 1/1991 | Sackner | 600/485 |
| 5,007,427 A | 4/1991 | Suzuki et al. | 600/436 |

(Continued)

FOREIGN PATENT DOCUMENTS

WO    WO 2005/115242    12/2005

(Continued)

OTHER PUBLICATIONS

Fahrenberg, "Origins and Developments of Ambulatory Monitoring and Assessment", in Fahrenberg et al., 2001, Progress in Ambulatory Assessment. Seattle, WA: Hogrefe and Huber.

(Continued)

*Primary Examiner* — Miranda Le
*Assistant Examiner* — Tiffany Weston
(74) *Attorney, Agent, or Firm* — Sterne, Kessler, Goldstein & Fox PLLC

(57) ABSTRACT

The invention provides a method for determining when a person is snoring by determining a candidate snore event by detecting the occurrence of a person's breath, and detecting the occurrence of a sound event. The method further includes confirming that the candidate snore event is not an isolated snore event by determining that breaths immediately preceding and following the candidate snore event include other candidate snore events.

25 Claims, 6 Drawing Sheets

U.S. PATENT DOCUMENTS

| | | | |
|---|---|---|---|
| 5,040,540 A | 8/1991 | Sackner | 600/485 |
| 5,074,129 A | 12/1991 | Matthew | 66/192 |
| 5,131,399 A | 7/1992 | Sciarra | 600/484 |
| 5,159,935 A | 11/1992 | Sackner et al. | 600/534 |
| 5,178,151 A | 1/1993 | Sackner | 600/485 |
| 5,301,678 A | 4/1994 | Watson et al. | 600/534 |
| 5,331,968 A | 7/1994 | Williams et al. | 600/534 |
| 5,348,008 A | 9/1994 | Bornn et al. | 600/301 |
| 5,353,793 A | 10/1994 | Bornn et al. | 600/386 |
| 5,416,961 A | 5/1995 | Vinay | 28/165 |
| 5,447,164 A | 9/1995 | Shaya et al. | 600/523 |
| RE35,122 E | 12/1995 | Corenman et al. | |
| 5,533,511 A | 7/1996 | Kaspari et al. | 600/485 |
| 5,544,661 A | 8/1996 | Davies et al. | 600/513 |
| 5,564,429 A | 10/1996 | Bornn et al. | 600/508 |
| 5,588,425 A | 12/1996 | Sackner et al. | 600/523 |
| 5,820,567 A | 10/1998 | Mackie | 600/519 |
| 5,899,855 A | 5/1999 | Brown | 600/301 |
| 5,913,830 A | 6/1999 | Miles | 600/535 |
| 5,989,193 A | 11/1999 | Sullivan | |
| 5,991,922 A | 11/1999 | Banks | 2/69 |
| 6,015,388 A | 1/2000 | Sackner et al. | 600/529 |
| 6,047,203 A | 4/2000 | Sackner et al. | 600/388 |
| 6,066,093 A | 5/2000 | Kelly et al. | 600/386 |
| 6,067,462 A | 5/2000 | Diab et al. | 600/310 |
| 6,139,505 A * | 10/2000 | Murphy | 600/532 |
| 6,142,953 A | 11/2000 | Burton et al. | 600/534 |
| 6,223,072 B1 | 4/2001 | Mika et al. | 600/510 |
| 6,254,552 B1 | 7/2001 | Lewis et al. | 600/3 |
| 6,273,859 B1 | 8/2001 | Remmers et al. | 600/529 |
| 6,341,504 B1 | 1/2002 | Istook | 66/172 E |
| 6,413,225 B1 | 7/2002 | Sackner et al. | 600/529 |
| 6,449,504 B1 | 9/2002 | Conley et al. | 600/523 |
| 6,551,252 B2 | 4/2003 | Sackner et al. | 600/536 |
| 6,604,115 B1 | 8/2003 | Gary et al. | 707/104.1 |
| 6,633,772 B2 | 10/2003 | Ford et al. | 600/345 |
| 6,721,594 B2 | 4/2004 | Conley et al. | 600/523 |
| 6,727,197 B1 | 4/2004 | Wilson et al. | 442/301 |
| 6,783,498 B2 | 8/2004 | Sackner et al. | 600/481 |
| 7,850,619 B2 * | 12/2010 | Gavish et al. | 600/538 |
| 2003/0135127 A1 | 7/2003 | Sackner et al. | 600/536 |
| 2004/0249299 A1 | 12/2004 | Cobb | 600/538 |
| 2005/0054941 A1 | 3/2005 | Ting et al. | 600/481 |
| 2005/0119586 A1 * | 6/2005 | Coyle et al. | 600/538 |
| 2005/0211247 A1 | 9/2005 | Noda et al. | 128/204.23 |
| 2005/0228234 A1 | 10/2005 | Yang | 600/529 |
| 2005/0240087 A1 | 10/2005 | Keenan et al. | 600/300 |
| 2006/0036183 A1 | 2/2006 | Sackner et al. | 600/324 |
| 2006/0178591 A1 * | 8/2006 | Hempfling | 600/529 |

FOREIGN PATENT DOCUMENTS

WO    WO 2006/002338    1/2006

OTHER PUBLICATIONS

International Search Report and Written Opinion of the International Searching Authority, PCT/US2007/070466, dated Mar. 24, 2008.

* cited by examiner

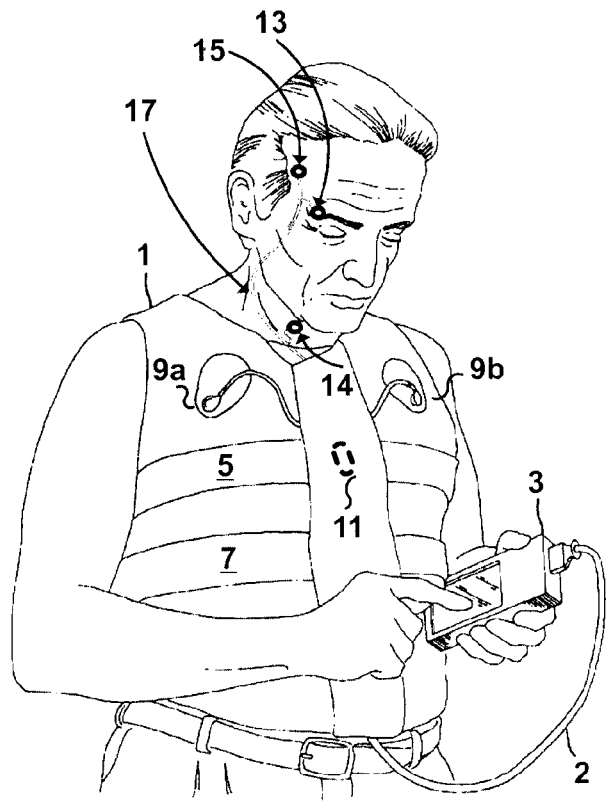
FIG. 1
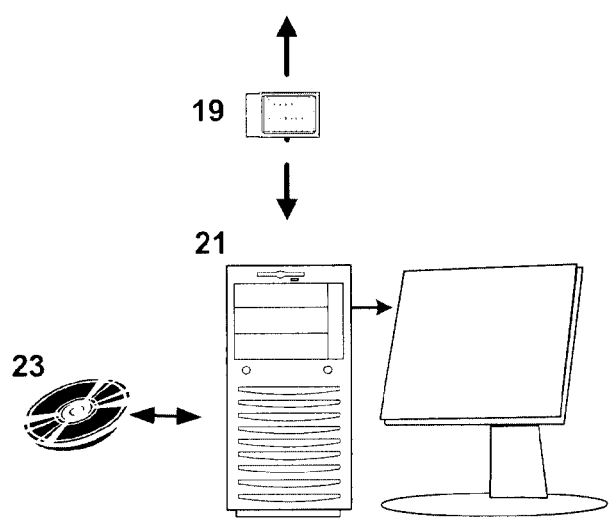

SYSTEM AND METHOD FOR SNORE DETECTION AND CONFIRMATION

1. CROSS-REFERENCE TO RELATED APPLICATIONS

This application claims the benefit of U.S. Provisional Application No. 60/811,777, filed on Jun. 8, 2006 the entire content of which is expressly incorporated herein by reference thereto.

2. FIELD OF THE INVENTION

The present invention relates to a system and method for real-time physiological monitoring, particularly of a sleeping person. More particularly, the invention relates to detecting when a person is snoring during sleep using a rule-based method.

3. BACKGROUND OF THE INVENTION

Methods of treatment and prevention of snoring are inherently not conducive to self-medication or self-administration due to the fact that a person who is snoring is necessarily asleep. As such, a person who is snoring typically must rely on another party to detect when that person is snoring so that a treatment or medication may be administered to prevent or substantially reduce the reoccurrence of snoring.

Auto-medication or auto-administration methods of treating or preventing snoring typically require a system that automatically detects when a person is snoring, and then automatically administers a prevention or treatment remedy. For example, a remedy may include inducing the person to adjust his or her physical posture, or locally administering a medication, preferably in or near the person's oral cavity, to prevent or substantially reduce continued snoring.

International Application No. WO 2006/002338A2, which was published Jan. 5, 2006 and which is incorporated herein in its entirety for all purposes by reference thereto, describes systems and methods for monitoring persons during sleep by recording respiratory and sound data to recognize cough-arousal events. The reference also describes administering an anti-tussive therapeutic agent to a person when a cough-arousal event is recognized. With respect to cough recognition, the reference describes monitoring using a monitoring garment comprising sensors that provide respiratory signals, sound signals, and EEG signals from a person; and a computer system comprising a computer readable memory comprising encoded instructions for receiving said sensor signals, which are processed in order to recognize cough events. Respiratory data and signals are preferably obtained from sensors that process a person's tidal volumes. Sound data and signals are preferably obtained from a sensor that is in contact with, or in close proximity to, the person's throat.

Prior automatic snore detection systems are relatively inaccurate and imprecise with respect to distinguishing an actual snore event from background noise or other artifacts that may originate from a person during sleep. This may result in unnecessarily triggering the administration of a prevention or treatment remedy. In light of these false-positive events, there remains a need for an automatic method and system for more accurately and precisely detecting the occurrence of snoring while a person is sleeping.

4. SUMMARY OF THE INVENTION

The present invention is directed to systems and computer-implemented methods of detecting and confirming occurrences of snore events while a person is sleeping. A preferred method includes determining a candidate snore event, which preferably includes detecting the occurrence of a person's breath and detecting the occurrence of a sound event. The preferred method also includes confirming that the candidate snore event is not an isolated snore event, preferably by determining that breaths immediately preceding and following the candidate snore event include other candidate snore events.

In one embodiment, the occurrence of a breath is detected when the person's breath has a volume that is less than a breath threshold. For example, the breath threshold is preferably about 1.25 liters. In other embodiments, the breath threshold can be higher or lower, depending on the desired sensitivity of the detection method.

In one embodiment, detecting the occurrence of a sound event includes sampling sound energy by measuring sound energy in the vicinity of a person's mouth and nose. Preferably, the sampled sound energy is the mean of at least 30 sound energy samples that are sampled at frequency of about 1500 Hz. The occurrence of a sound event is preferably detected when the sampled sound energy is greater than a sound event threshold and lasts longer than a sound event period. For example, the sound event period is preferably about 50 milliseconds.

In another embodiment, the occurrence of a sound event is detected when a peak sound energy occurrence ratio is greater than a threshold ratio. Preferably, the peak sound energy occurrence ratio is the temporal location of the peak sound energy expressed as a fraction relative to the total duration of the sampled sound energy. More preferably, the threshold ratio is about 10%.

In yet another embodiment, the occurrence of a sound event is determined to be a candidate snore event when the pitch of the sampled sound energy is greater than a minimum pitch and less than a maximum pitch. Preferably, the minimum pitch is about 14 and the maximum pitch is about 28.

In still yet another embodiment, a sound event is labeled as a candidate snore event when the fraction of the sampled sound energy that occurs during inspiration is greater than an inspiration threshold. Preferably, the inspiration threshold is about 80%.

In other embodiments, the occurrence of a sound event can be detected and confirmed using combinations of any of the above methods, or other methods as generally known.

Preferably, confirmation that a candidate snore event is not an isolated snore event is achieved by processing at least five breaths immediately preceding and following the candidate snore event, and then detecting other candidate snore events in at least three of the at least five preceding or following breaths.

In another embodiment, a candidate snore event is confirmed as an isolated snore event by processing at least seven breaths immediately preceding and following the candidate snore event, and then classifying the candidate snore event as an isolated snore event if none of the at least seven breaths immediately preceding and following the candidate snore event includes another candidate snore event.

The present invention also provides systems having a processor coupled to a computer-readable memory, where the computer-readable memory has instructions for causing the processor to perform any of the methods of this invention. The present invention also provides monitoring systems comprising comfortable, ambulatory monitoring garments for providing respiratory and sound data to systems of this invention. The present invention also provides program products having a computer-readable memory, where the computer-readable memory has instructions for causing the processor to perform any of the methods of this invention.

The present invention thus provides a method of automatically detecting, with increased accuracy and precision, the occurrence of snore events while a person is sleeping.

5. BRIEF DESCRIPTION OF THE DRAWINGS

The present invention may be understood more fully by reference to the following detailed description of preferred embodiments of the present invention, illustrative examples of specific embodiments of the invention, and the appended figures in which:

FIG. 1 illustrates an embodiment of a wearable monitoring device and associated processing system;

6. DETAILED DESCRIPTION OF THE PREFERRED EMBODIMENTS

Figure 2:
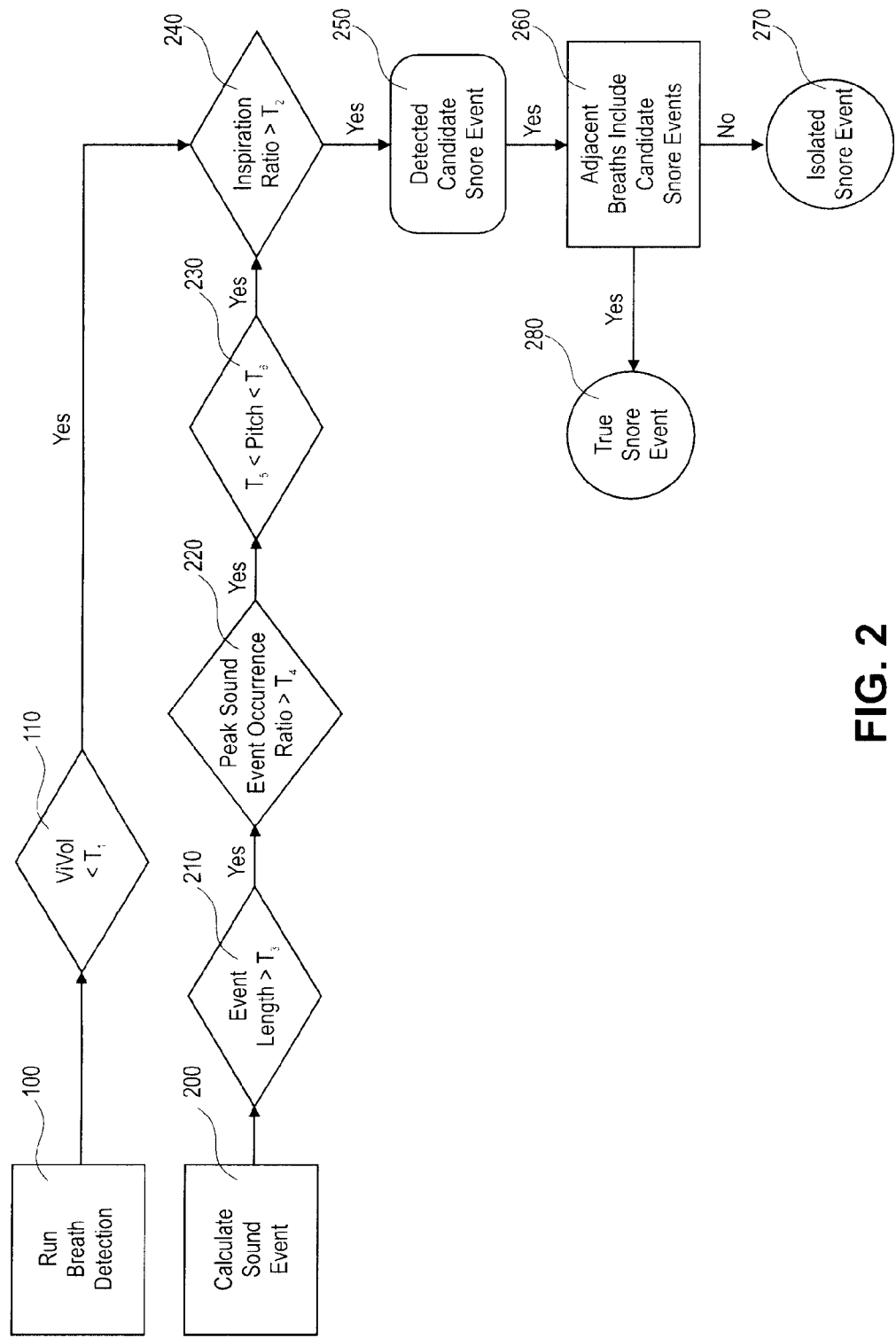
FIG. 2 illustrates an embodiment of a candidate snore event detection and confirmation method of the present invention.

The present invention is directed to a system and method of detecting and confirming occurrences of snore events while a person is sleeping. Preferred methods of detection and confirmation of snore events are described, as well as preferred monitoring systems used to implement such methods.

6.1 Preferred Monitoring Systems

Preferably, the physiological monitoring systems are ambulatory systems configured so that a person is not constrained while sleeping. Preferably, the ambulatory monitoring systems are also configured for use without assistance by medical or other trained personnel. A preferred ambulatory physiological monitoring system configuration includes a wearable item, for example, a garment, band, patch, and the like, or associations with partial-shirts or shirts, on partial body suits, or in full body suits that are unobtrusive, comfortable, and preferably made of non-restricting fabric into which sensors are incorporated.

A preferred embodiment of an ambulatory monitoring systems is illustrated in FIG. 1, which depicts garment or shirt 1, which is preferably sufficiently comfortable and unobtrusive so that a person's sleep is substantially not disturbed. Garment 1 carries, or has embedded or integrally included therein sensors for gathering necessary monitoring data, and permits physiological recording during sleep, preferably in a home setting of up to at least about a full night's duration.

In one embodiment, the garment is the LIFESHIRT® ambulatory monitoring garment made by Vivometrics, Inc. (Ventura, Calif.). Such a garment is a preferred example of the monitoring equipment used to collect and provide data for the present invention. Such disclosure, however, does not limit the invention, and in other embodiments, the data processed by this invention can be gathered by other sensor technologies known in the art, and by other dispositions and arrangements of such sensors on the monitored person. However, for conciseness only, the following description is largely in terms of this preferred embodiment of the monitoring garment and associated system components.

The garment 1 preferably includes size sensors, and more preferably, the sensors include inductive plethysmographic (IP) sensor bands 5 and 7 (or other sensor types providing respiratory rate and volume information), one or more accelerometers and the like for sensing body posture and motion, for example exemplary accelerometer 11, and one or more microphones for detecting sound, such as throat microphone 14. Garment 1 is preferably made of a stretchable material that fits sufficiently snugly to expand and contract with a person's body so that embedded IP sensor bands (which, for respiratory measurement, are known as respiratory inductive plethysmographic, or RIP, bands) can measure cross-sectional areas or circumferences of the person's torso. One RIP band is adequate, but preferably two RIP bands are used: band 5 at the level of the rib cage, and band 7 at the level of the abdomen.

"Size sensors" gather signals responsive to size indicia describing portions of a monitored person's body, e.g., the torso, the neck, the extremities, or parts thereof. Size indicia can include the length along a selected portion of the body surface; the circumference, diameter, or cross-sectional area of a body part; and the like.

Size sensor signals can also be processed to yield information about organ system functioning. Signals from size sensors at one or more levels of the torso, e.g., at an abdominal level and at a rib cage level, can be interpreted using a two-component breathing model in order to determine respiratory rates, respiratory volumes, respiratory events, and the like. U.S. Pat. Nos. 6,551,252; 5,159,935; and 4,777,962, and U.S. patent application Ser. No. 10/822,260, which are incorporated herein in their entireties for all purposes by reference thereto, describe such signal processing.

Additional sensors, optional for this invention, may be in or in communication with the garment 1, and include pulse oximeters, capnographs, EEG electrodes (illustrated as 9a and 9b), and the like. EMG and EOG signals can be obtained from EEG and EOG sensors that are also preferably included in the garment 1, such as single bipolar (parietally-located) EEG sensor 15 and single-lead EOG sensor 13. The EEG and EOG sensors are preferably in electrical communication with garment 1, for example by means of conductive connector 17. In the hospital, clinic, or laboratory settings, other signals may be obtained from a wide range of physiological sensors.

Associated locally with preferred garment 1 is local data recording unit 3 operatively connected to sensors of the garment 1 by data cable 2. In other embodiments, the recording unit may be operatively connected to the sensors using means, for example, by short range radio link. Data recording unit 3 is preferred for ambulatory use, and is preferably compact and lightweight so that it can be worn on a belt, put in a pocket, or embedded in garment 1. This unit stores sensor data with sufficient accuracy and precision for full medical disclosure and off-line analysis, and may include a touch screen or other user input facility for implementing a digital diary whose data may also be transferred to the analysis computer for correlation with sensor readings.

Initial sensor signal processing generally includes filtering, digitization, noise limiting, extraction of relevant signal components, and the like. Following initial processing, specific processing of respiratory size sensor signals and microphone sound data signals are preferably performed to identify snores according to the methods of this invention. For example, processing respiratory signals includes calibration, determination of a tidal volume signal, and extraction of respiratory events from the tidal volume signal. U.S. Pat. Nos. 6,413,225;

5,159,935; 4,834,109; and 4,777,962, and U.S. patent application Ser. No. 10/822,260 filed Apr. 9, 2004, all of which are incorporated herein in their entirety for all purposes by reference thereto, describe such respiratory processing.

In one embodiment, basic signal processing, e.g. filtering and digitization, is performed on the data recording unit 3. This unit may have sufficient processing capability (e.g., a microprocessor or FPGA or the like) to also perform the methods of this invention and record identifies snores. The methods of the present invention may also be implemented by analysis software that is executed on analysis computers, such as computer 21, that may be remotely located. Analysis can be done either concurrently with signal recording (online) or at a later time (offline). For offline analysis, sensor data can be transferred from data recording unit 3 to analysis computer 21 on memory card 19, such as a compact flash card. Data may alternatively be transferred by wireless links, such as transmission using cell phone technologies and the like.

The methods of the present invention are performed on software or firmware programmable systems. In the case of software programming, methods are preferably coded in standard computer languages, such as C, C++, or in high level application languages, such as Matlab and associated toolboxes (MathWorks, Natick, Mass.). Code is then translated or compiled into executable computer instructions for controlling a microprocessor or similar device. In the case of firmware programming, higher level method specifications written in software languages or hardware languages such as VHDL, are preferably translated into bit codes by tools supplied by the manufacturer of the hardware part that is being programmed. For example, manufacturer's tools prepare bitstreams for configuring FPGAs.

All or part of this analysis software implementing this invention's methods may be made available as a program product on a computer readable medium, such as optical disk 23.

6.2 Preferred Snore Detection Methods

The present invention preferably includes methods and systems of determining whether a person is snoring by detecting and confirming the occurrence of a true snore event. In general, preferred methods detect a candidate snore event by monitoring a person to determine an occurrence of sound event of an appropriate energy, duration, shape, and pitch that is characteristic of a true snore. Additionally, the method preferably determines whether such an occurrence of sound is also coincident with a non-artifact, inspiratory event. Once a candidate snore event is detected, it is confirmed as a true snore event by determining whether or not it occurs in isolation or among a series of other snore events.

In a preferred embodiment, the method for determining when a person is snoring includes determining a candidate snore event by detecting the occurrence of a person's breath and detecting the occurrence of a sound event. The preferred method also includes confirming that the detected candidate snore event is not an isolated snore event by determining that breaths immediately preceding and following the candidate snore event include other candidate snore events.

Preferably, the method of detecting a candidate snore event includes using a rule-based method. Sound events that are related to snore events typically occur during inspiration, and a rule-based method advantageously enables a more accurate and precise differentiation of a candidate snore event from background noise, artifact inspirations, or other interference. A preferred detection method using a rule-based method is illustrated in FIG. 2. As embodied herein, the method preferably includes various components for detecting breath occurrences and sound events to determine a candidate snore event.

Preferably, a component for detecting true breath occurrences includes identifying inspirations by calculating their beginnings and ends. Such identification is preferably performed by using a breath detection method 100, for example, as described in U.S. Application Publication No. 2004/0249299, which is incorporated herein in its entirety for all purposes by reference thereto. The method includes monitoring a person's breathing using sensors, preferably IP size sensors disposed about the person's torso as described above, and processing the signals and data relating to tidal volumes and inspired volumes to produce a tidal volume trace ("$V_t$") and an inspired volume trace ("ViVol"). Motion artifact or other interferences typically result in the detection of unusually large breaths that are beyond physiological limits. To limit the inclusion of such tainted breaths during determination of breath occurrences, the method preferably requires that the measured breath have a volume that is less than a breath threshold $T_1$ in order for a breath to be detected as a breath occurrence, as shown in step 110.

The breath threshold $T_1$ is preferably selected from empirical data based on histograms or other distributions of known volumes of true breath occurrences as well as artifact breaths. Preferably, such data is representative of a large population of persons and adjusted for different physical parameters, such as age, height, weight, and gender. In one embodiment, the breath threshold $T_1$ is selected for each individual person based on probability distributions of collected breath volumes for that person. In other embodiments, the breath threshold $T_1$ can be set higher or lower, depending on the desired sensitivity of the detection method. Preferably, the breath threshold $T_1$ is between about 1 liter and about 2 liters, and more preferably, the breath threshold $T_1$ is about 1.5 liters. In a preferred embodiment, the breath threshold is about 1.25 liters.

Figure 3:
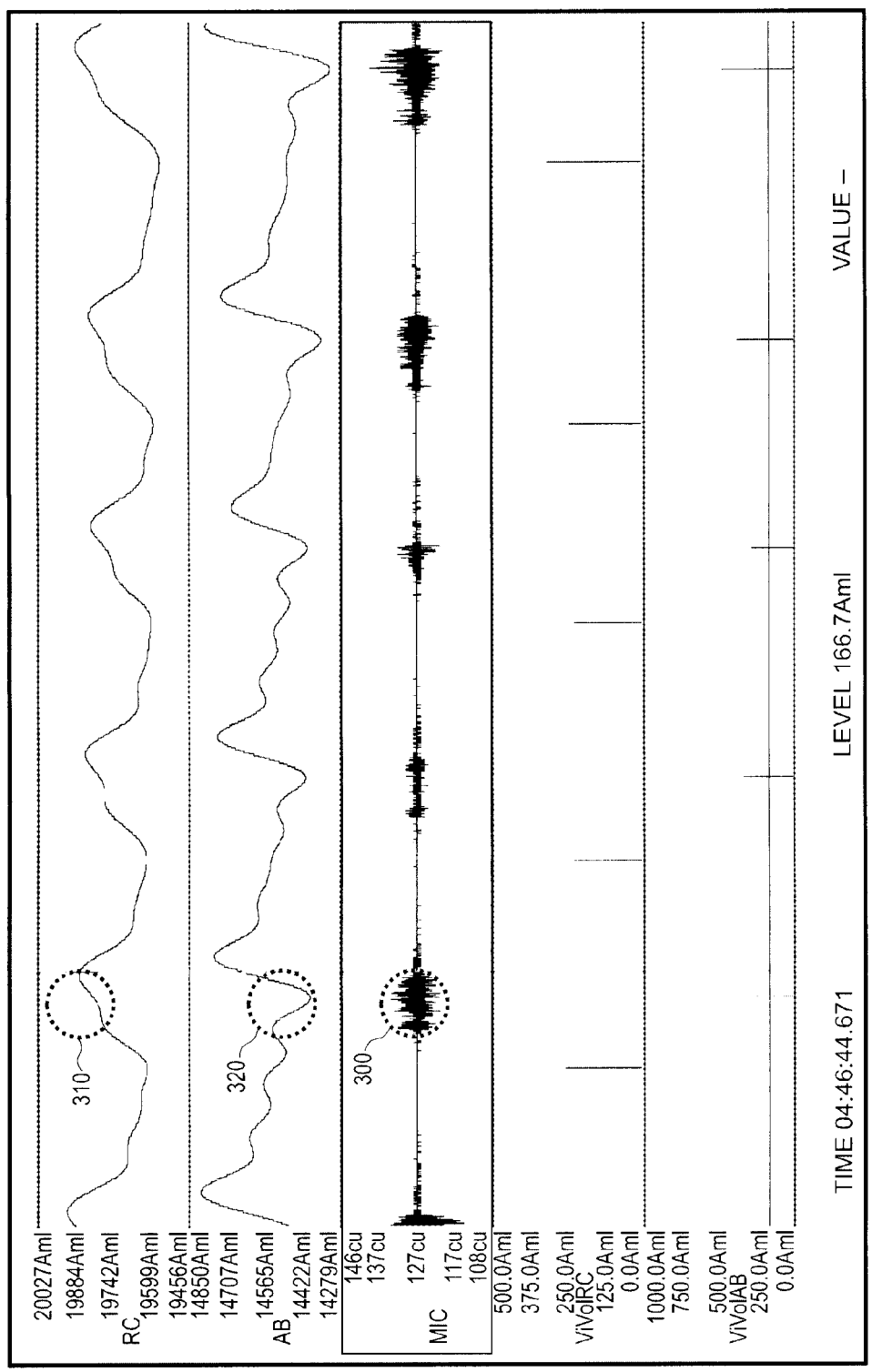
FIG. 3 illustrates an embodiment of monitoring data showing asynchrony in the RC and AB traces.

In some instances, for example in patients who exhibit upper airway obstructions, asynchrony may be found between the ribcage (RC) and abdominal (AB) compartments/signals when the patient is monitored during snoring. Such an asynchrony can be seen in the traces of FIG. 3, where the portion 300 of the microphone trace ("MIC") occurs during the inspiratory portion 310 of the RC trace, but during the end of the expiratory and beginning of the inspiratory portion 320 of the AB trace. Because the RC and AB signals are summed to form the $V_t$ trace, the asynchrony between the data may result in snore events that do not always fall on inspiration, and therefore some snore events could be undetected when using breath detection methods based on the $V_t$ trace alone. As such, an alternative breath detection method includes processing the AB and RC signals separately to mark the beginnings and ends of inspiration. In this way, sound events, and thus potential candidate snore events, can be marked on inspiration independently for both the RC signal and the AB signal. This preferably ensures that possible candidate snore events will not be unaccounted for due to asynchrony in the RC and AB signals.

Another alternative breath detection method can further include filtering or smoothing the RC and AB traces, such as by high-pass filtering the traces between about 0.15 and 0.5 Hz, for example. The averaged energy of these waveforms can be obtained, for example by squaring the amplitude of the resultant trace, over the duration of the sound event. A snore event typically will have a greater high frequency contribution than a non-snore event, and thus the method can include identifying a true breath occurrence when the averaged energy is greater than a pre-determined threshold energy.

In addition to detecting a true breath occurrence, the method 200 for determining a candidate snore event embodied in FIG. 2 also includes components for detecting the occurrence of a sound event. Preferably, sound energy is sampled using a microphone or other sound recorder disposed in the vicinity of a person's mouth and nose, for example near a person's throat. In one embodiment, the microphone is first used to extract one or more of the following parameters, for example, and create associated traces from a provided audio sample: 1) sound envelope, 2) sound event or event marker, 3) pitch, 4) sound energy, 5) duration, and 6) peak fraction or ratio.

Initially, signals and data corresponding to sampled sound energy from the microphones are processed to produce the MIC trace. Preferably, sound energy is derived from the MIC trace by sampling at frequencies between about 1000 Hz and about 2000 Hz. Sound energy can be processed to produce a sound energy trace ("SE"), for example, by normalizing and summing the absolute values of the microphone samplings over a range of samples, preferably between about 20 and 40 samples. In a preferred embodiment, a 50 Hz SE trace is produced by sampling at about 1500 Hz and summing the absolute values of the microphone samplings for every 30 samples.

A sound event trace ("EVT") is then preferably produced using the SE trace to determine when a sound event occurs. Preferably, the EVT trace is a binary trace at the same resolution as the SE trace, and sound energy is the integral of the SE trace over the duration of the EVT event. The EVT trace is deemed ON, i.e. it detects a sound event, when the SE trace first exceeds an upper sound event threshold $T_{USE}$ and lasts for at least a sound event period $T_3$ before turning OFF when the SE trace drops below a lower sound event threshold $T_{LSE}$. In one embodiment, the upper sound event threshold $T_{USE}$ is calculated as twice the noise threshold, or between about 50 and 70, and the lower sound event threshold $T_{LSE}$ is between about 20 and 40. The units for the $T_{USE}$ and $T_{LSE}$ values are preferably based on an 8 bit sampled signal from the microphone, which is rectified and summed to get the SE trace. As such, the actual units are relative and un-calibrated, and simply refer to the quantization of the signal.

Preferably, the $T_{USE}$ and $T_{LSE}$ values are selected from empirical distributions of quiescent baseline noise and sound values. The values can be set relatively low so as to be sensitive to most sounds, but can also be varied higher or lower depending on the desired sensitivity of the detection method and background noise. The noise threshold is preferably calculated over a period of at least about 240 hours of microphone recordings and is determined by monitoring a signal variation between +1 and −1. In a preferred embodiment, a sound event is detected when the EVT trace exceeds a $T_{USE}$ of about 60 for a selected sound event period $T_3$ before dropping below a $T_{LSE}$ of about 30, for three consecutive samples.

The duration of a sound event is the length, for example in milliseconds, of the EVT ON period, i.e., the length of the SE trace between the $T_{USE}$ and $T_{LSE}$ thresholds. In one embodiment, for example, the EVT trace must preferably exceed the upper sound event threshold $T_{USE}$ for at least the duration of a sound event period $T_3$ before dropping past the lower sound event threshold $T_{LSE}$ in order for the method to detect a sound event, as shown in step 210. $T_3$ is preferably based on empirical distributions of durations of true snore events, and the threshold can be varied depending on the desired sensitivity of the detection method. Preferably, the sound event threshold $T_3$ is between about 40 ms and 60 ms, and more preferably, $T_3$ is about 50 ms.

As shown in FIG. 2, another component for determining a sound event can also preferably include analysis of the shape of the EVT trace. A true snore event tends to continuously rise in volume until a peak volume is attained, usually near the end of the snore event. The temporal location of the peak volume of the SE trace during the entire duration of a sound event is preferably calculated and expressed as a fraction of the entire sound event duration, i.e., as a peak sound event occurrence fraction or ratio. For example, the peak sound event occurrence ratio refers to the peak of the SE trace for each sound event expressed as a fraction of the total EVT duration (Peak location−Start)/(End−Start). If a single sound event includes multiple instances of the same peak volume, then the location of the first peak volume is preferably used in the calculation of the peak sound event occurrence ratio. Typically, this fraction or peak sound event occurrence ratio will never be below about 10%-20% for a true snore event. Thus, one embodiment of the method requires that in order for a sound event to be detected, the peak sound event occurrence ratio must exceed a threshold ratio $T_4$, as shown in step 220, $T_4$ preferably being not less than about 10%, and more preferably not less than about 20%. Similar to the other thresholds described above, the threshold ratio $T_4$ is preferably selected based on empirical distributions and histograms of peak volumes of known snore events, and may be adjusted based on the desired sensitivity of the detection method.

Another component of the preferred candidate snore event detection method shown in FIG. 2 includes analysis of the pitch of the sampled sound energy. A true snore event typically has a narrow pitch range that is characteristic thereof. As such, one embodiment of the method includes determining whether the sampled sound energy falls between a minimum pitch $T_5$ and a maximum pitch $T_6$, as shown in step 230. Preferably, the minimum pitch $T_5$ is between about 10 and 20 and the maximum pitch $T_6$ is between about 25 and 35, and more preferably, $T_5$ is about 14 and $T_6$ is about 28. Similar to the $T_{USE}$ and $T_{LSE}$ values, the units of minimum and maximum pitch are relative to the computer units that the microphone is sampled at and thus are not absolute. The minimum and maximum pitches are preferably selected based on empirical distributions and histograms of pitch ranges of known snore events, and in other embodiments may be adjusted based on the desired sensitivity of the detection method.

The pitch of a sound event is preferably evaluated using the Mel cepstrum of the raw MIC trace. A cepstrum is the result of taking the Fourier Transform (FT) of the decibel spectrum as if it were a signal. The cepstrum is preferably defined as the FT of the log (with unwrapped phase) of the FT (cepstrum of signal=FT(log(FT(the signal))+j2πm), where m is the integer required to properly unwrap the angle of the complex log function.

There is a real cepstrum and a complex cepstrum. The real cepstrum preferably uses the logarithm function defined for real values, while the complex cepstrum uses the complex logarithm function defined for complex values as well. The complex cepstrum holds information about magnitude and phase of the initial spectrum, allowing reconstruction of the signal. The real cepstrum only uses the information of the magnitude of the spectrum.

The cepstrum is an excellent feature vector for representing the human voice. For such applications, the spectrum is preferably first transformed using the Mel frequency bands. The result is called the Mel Frequency Cepstral Coefficients (MFCC), and can be used for voice identification, pitch detection and other analysis. This is a result of the cepstrum advantageously separating the energy resulting from vocal cord vibration from the "distorted" signal formed by the rest of the vocal tract.

FIG. 2 also includes a component that combines the input of breath and sound signals and data to determine the fraction of the sound event that occurs during inspiration. Typically, about 80%-100% of a true snore event occurs during inspiration, with the remaining portion of the snore event occurring during expiration. As such, one embodiment of the preferred method includes determining what portion of the sampled sound event occurs during inspiration, and whether such portion, expressed as a ratio with respect to the duration of the entire sound event, is greater than an inspiration threshold $T_2$, as shown in step 240. Preferably, the inspiration threshold $T_2$ is at least about 80%, and more preferably is at least about 90%. Such a threshold is preferably selected based on empirical distributions and histograms of inspiration fractions of known snore events, and in other embodiments may be adjusted based on the desired sensitivity of the detection method.

The method for detecting a candidate snore event may include all of the components described above, and illustrated in the embodiment of FIG. 2, or may include a single component or a combination of one or more components. Such a selection of components may be made in accordance with the desired sensitivities of the detection method, or based on the physical characteristics of the person being monitored. Additionally, other embodiments of the snore detection method can include the use of standard and known pattern recognition approaches, for example using a machine learning approach or other pattern recognition approaches such as described in Duda et al., 2000, Pattern Classification (2nd edition), Wiley-Interscience, which is incorporated herein in its entirety for all purposes by reference thereto, rather than a rule-based method.

Once a candidate snore event is determined, for example as shown in step 250, the preferred method of determining a true snore event also includes confirming that the detected candidate snore event is a true snore event rather than an isolated snore event, as shown in step 260 of FIG. 2. Preferably, this is achieved by using a rule-based method for determining that breaths immediately preceding and following the candidate snore event include other candidate snore events.

Typically, a true snore event does not occur in isolation. Rather, a true snore event is usually accompanied by other snore events that occur in successive breaths. As such, one embodiment of the preferred method includes monitoring and analyzing breath occurrences and sound events over a discrete time period, and marking identifying all candidate snore events within that period. The method then preferably includes scanning through all candidate snore events within the period, and determining the number of snore events that occur during neighboring breaths.

For example, for each candidate snore event, the method can require analysis of the 5 preceding breaths or 5 subsequent breaths, or both. If at least 3 out of the 5 preceding and subsequent breaths surrounding the examined candidate snore event also include other candidate snore events, then the method identifies the candidate snore event as not isolated, and thus a true snore event in step 280. If, on the other hand, less than 3 of the 5 preceding and subsequent breaths include other candidate snore events, then the candidate snore event is confirmed as an isolated snore event, as shown in step 270. Other variations of the confirmation method can include examination of more or less neighboring breaths, and other requirements as to the number of neighboring breaths that include candidate snore events, depending on the desired sensitivity of the detection method.

As an additional verification that the examined candidate snore event is not an isolated snore event, the confirmation method also preferably includes analysis of neighboring breaths and classifying the candidate snore event as isolated, and thus not a true snore event, if none of the neighboring breaths include another candidate snore event. The assumption is that snoring does not occur in isolation, and it is highly unlikely that several falsely identified candidate events will be labeled consecutively. For example, one embodiment of the confirmation method includes analysis of the 7 preceding breaths or of the 7 subsequent breaths, or both. If none of these preceding and/or subsequent breaths include a candidate snore event, then the examined candidate snore event is marked as isolated, as shown in step 270. On the other hand, if at least one of these preceding and/or subsequent breaths does in fact include another candidate snore event, then the examined candidate snore event is classified as a true snore event, as shown in step 280. As described above, other variations of the confirmation method can include examination of more or less neighboring breaths, and other requirements as to the number of neighboring breaths that include candidate snore events, depending on the desired sensitivity of the detection method.

6.3 EXAMPLES

The present invention for the detection of candidate snore events is illustrated by the following examples that are merely for the purpose of illustration and are not to be regarded as limiting the scope of the invention or the manner in which it can be practiced.

Figure 4:
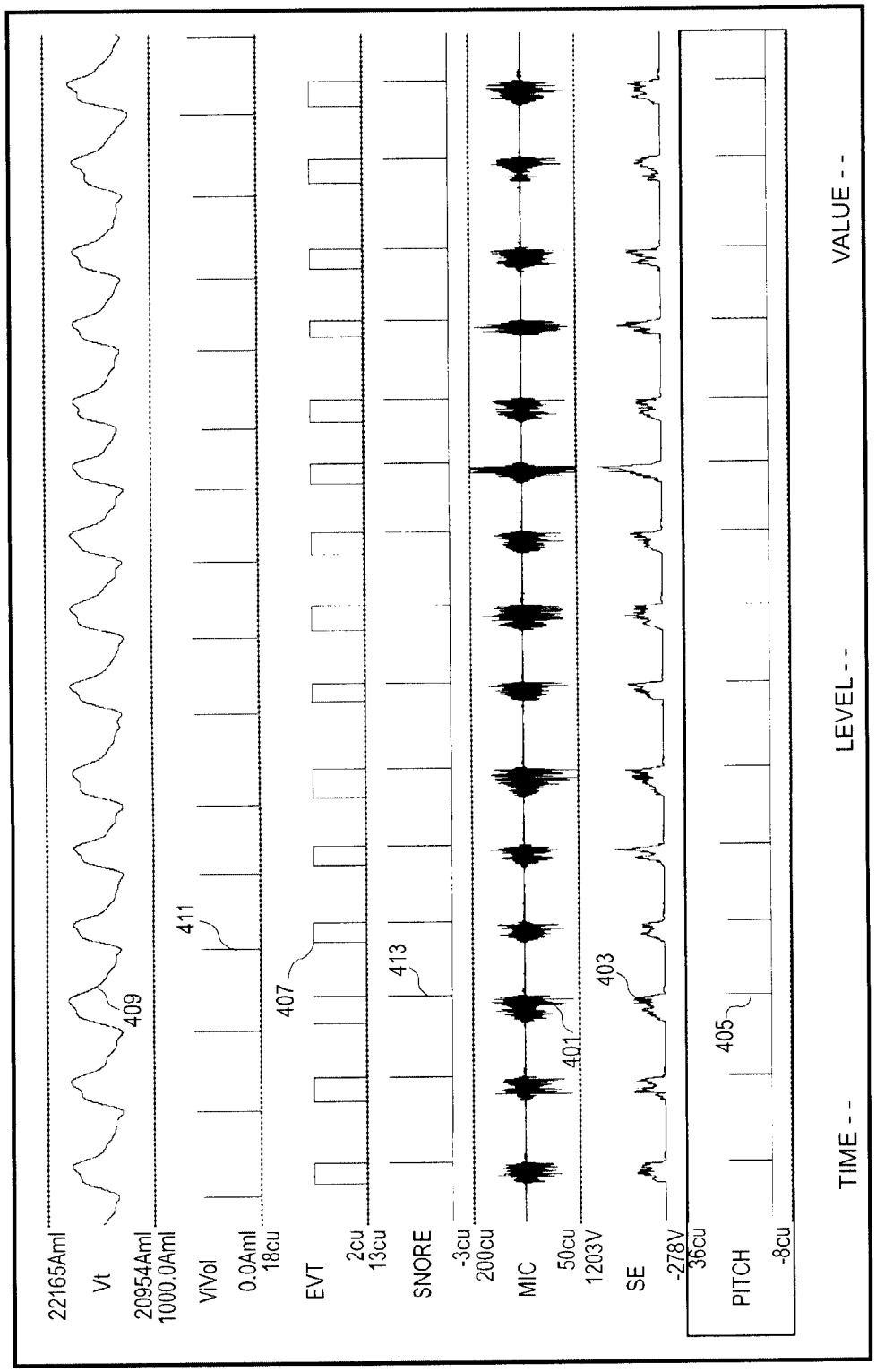
FIG. 4 illustrates a set of results of an embodiment of a method for detecting a candidate snore event.

FIG. 4 illustrates one embodiment of exemplary traces of a variety of snore detection signals and data as a function of time, including, from the top to the bottom of FIG. 4, a tidal volume trace ($V_t$) 409, an inspired volume trace (ViVol) 411, a sound event trace (EVT) 407, a snore trace (SNORE) 413, a microphone trace (MIC) 401, a sound energy trace (SE) 403, and a pitch trace (PITCH) 405. As described above, the preferred method of detecting a candidate snore event includes, for example, determining whether the ViVol 411 exceeds a breath threshold $T_1$, determining whether the EVT 407 exceeds a $T_{USE}$ for at least the duration of a sound event period $T_3$ before dropping past a $T_{LSE}$, and determining whether the PITCH 405 falls between a minimum pitch $T_5$ and a maximum pitch $T_6$. Compliance with one or more of these rules results in the detection of a candidate snore event in the SNORE trace 413.

Figure 5:
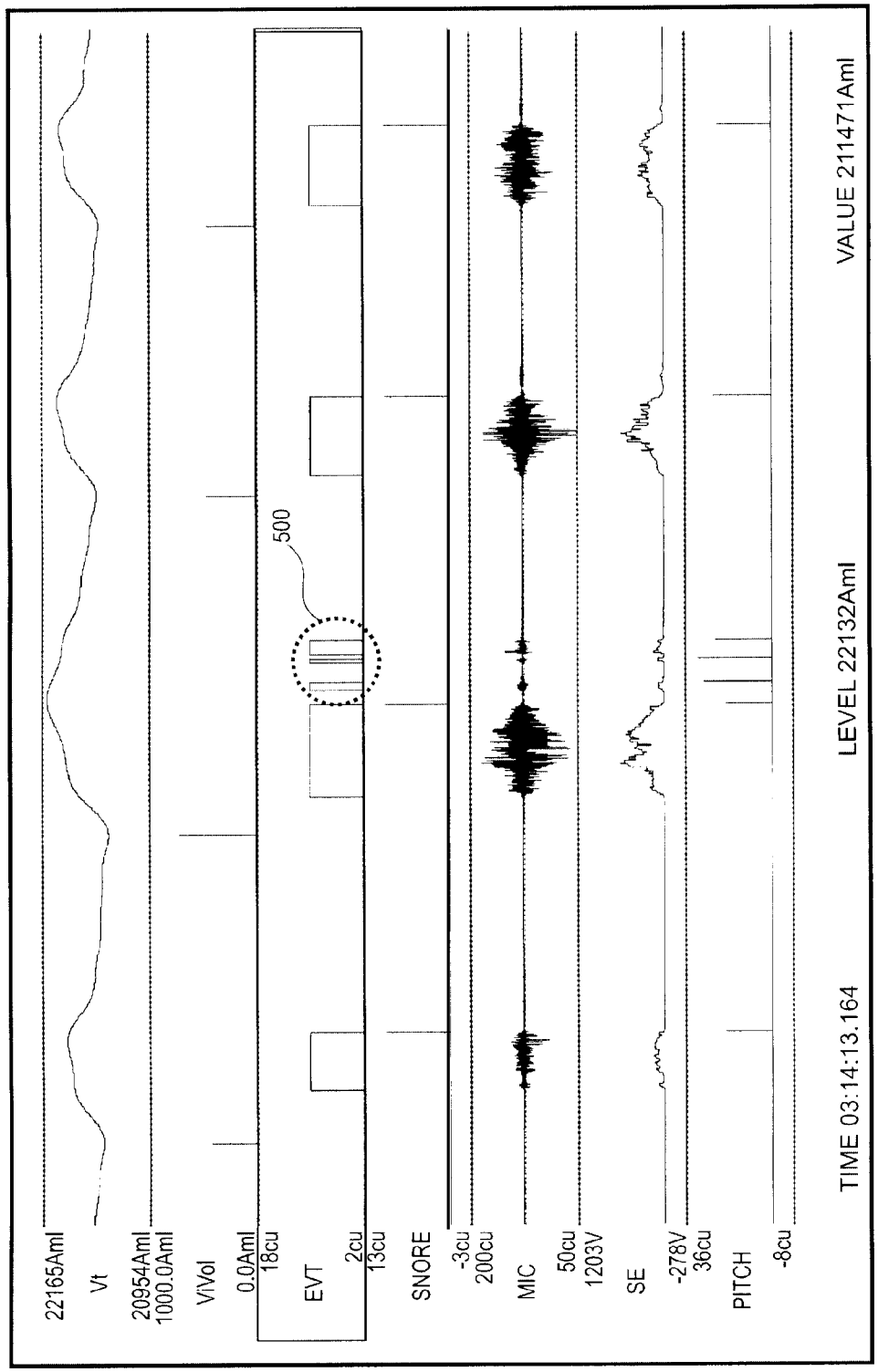
FIG. 5 illustrates another set of results of the embodiment thereof.

FIG. 5 illustrates another embodiment with the same exemplary traces of FIG. 4. As seen, for example, in portion 500 of the EVT trace, and corresponding portions of the SNORE, PITCH, $V_T$, MIC, and SE traces of FIG. 5, the snore detection method does not mark as candidate snore events those breaths that include relatively small expiratory events.

Figure 6:
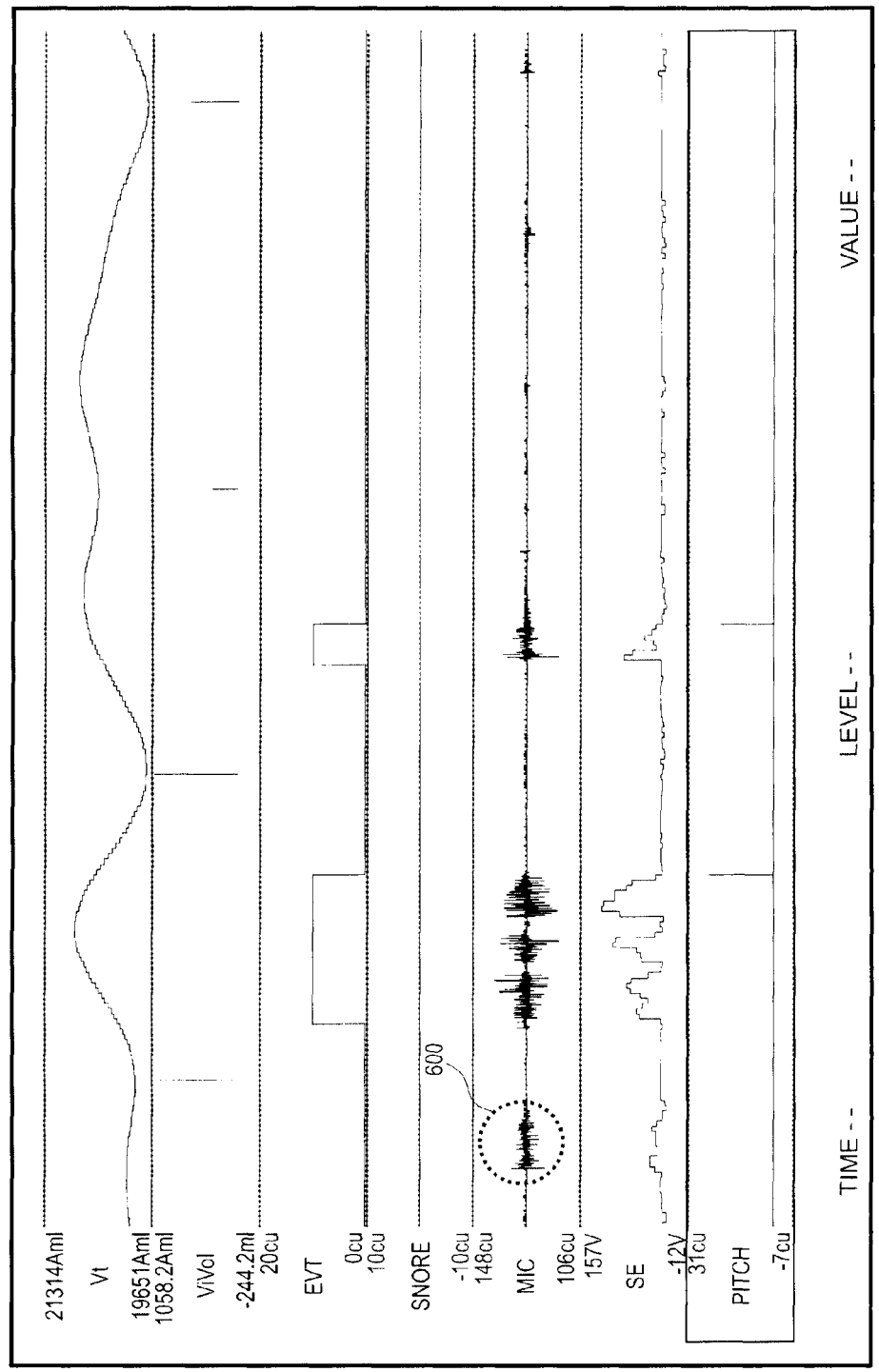
FIG. 6 illustrates yet another set of results of the embodiment thereof.

FIG. 6 illustrates another embodiment with the same exemplary traces of FIG. 4. FIG. 6 shows how speech or artifact that occur during inspiration, for example portion 600 of the MIC trace and corresponding portions of the EVT, SNORE, PITCH, and SE traces, are not detected as candidate snore events. Even though the microphone and sound energy traces indicate the occurrence of sound or noise upon inspiration, the snore trace does not identify such sound or noise as a candidate snore event.

The term "about," as used herein, should generally be understood to refer to both the corresponding number and a range of numbers. Moreover, all numerical ranges herein should be understood to include each whole integer within the range.

While illustrative embodiments of the invention are disclosed herein, it will be appreciated that numerous modifications and other embodiments can be devised by those of ordinary skill in the art. Features of the embodiments described herein can be combined, separated, interchanged, and/or rearranged to generate other embodiments. Therefore, it will be understood that the appended claims are intended to cover all such modifications and embodiments that come within the spirit and scope of the present invention.

A number of references are cited herein, the entire disclosures of which are incorporated herein, in their entirety, by reference for all purposes. Further, none of these references, regardless of how characterized above, is admitted as prior to the invention of the subject matter claimed herein.

What is claimed is:

1. A method for determining when a person is snoring, the method comprising:
   determining a candidate snore event, which comprises:
      detecting the occurrence of a person's breath using a sensor; and
      detecting the occurrence of a sound event by measuring sound energy using a microphone, wherein the occurrence of the sound event is detected when a peak sound energy occurrence ratio is greater than a threshold ratio, the peak sound energy occurrence ratio being the temporal location of the peak sound energy expressed as a fraction relative to the total duration of the sampled sound energy; and
   confirming that the candidate snore event is not an isolated snore event by determining that breaths immediately preceding and following the candidate snore event include other candidate snore events.

2. The method of claim 1, wherein the threshold ratio is about 10%.

3. The method of claim 1, wherein the occurrence of a breath is detected when the person's breath has a volume that is less than a breath threshold.

4. The method of claim 3, wherein the breath threshold is about 1.25 liters.

5. The method of claim 1, wherein measuring sound energy comprises measuring sound energy in the vicinity of a person's mouth and nose to sample sound energy.

6. The method of claim 5, wherein the sampled sound energy is the mean of at least 30 sound energy samples that are sampled at a frequency of about 1500 Hz.

7. The method of claim 5, wherein the occurrence of a sound event is detected when the sampled sound energy is greater than a sound event threshold and lasts longer than a sound event period.

8. The method of claim 7, wherein the sound event period is about 50 milliseconds.

9. The method of claim 7, wherein the occurrence of a sound event is determined to be a candidate snore event when the pitch of the sampled sound energy is greater than a minimum pitch and less than a maximum pitch.

10. The method of claim 9, wherein the relative minimum pitch is about 14 and the relative maximum pitch is about 28.

11. The method of claim 7, wherein the occurrence of a sound event is determined to be a candidate snore event when the fraction of the sampled sound energy that occurs during inspiration is greater than an inspiration threshold.

12. The method of claim 11, wherein the inspiration threshold is about 80%.

13. The method of claim 1, wherein a candidate snore event is confirmed as not an isolated snore event by:
   processing at least five breaths immediately preceding and following the candidate snore event, and
   detecting other candidate snore events in at least three of the at least five preceding or following breaths.

14. The method of claim 13, further comprising:
   processing at least seven breaths immediately preceding and following the candidate snore event, and
   classifying the candidate snore event as an isolated snore event if none of the at least seven breaths immediately preceding and following the candidate snore event includes another candidate snore event.

15. The method of claim 1, wherein the detecting and confirming of candidate snore events is computer-implemented.

16. A system for determining a snore event comprising:
   a processor; and
   a computer readable memory operatively coupled to the processor and configured with instructions for causing the processor to perform a method for determining when a person is snoring, the method comprising:
   determining a candidate snore event, which comprises:
      detecting the occurrence of a person's breath using a sensor; and
      detecting the occurrence of a sound event by measuring sound energy using a microphone, wherein the occurrence of the sound event is detected when a peak sound energy occurrence ratio is greater than a threshold ratio, the peak sound energy occurrence ratio being the temporal location of the peak sound energy expressed as a fraction relative to the total duration of the sampled sound energy; and
   confirming that the candidate snore event is not an isolated snore event by determining that breaths immediately preceding and following the candidate snore event include other candidate snore events.

17. A monitoring system for determining a snore event comprising:
   a processor;
   a computer readable memory operatively coupled to the processor and configured with instructions for causing the processor to perform a method for determining when a person is snoring, the method comprising:
   determining a candidate snore event, which comprises:
      detecting the occurrence of a person's breath using a sensor; and
      detecting the occurrence of a sound event by measuring sound energy using a microphone, wherein the occurrence of the sound event is detected when a peak sound energy occurrence ratio is greater than a threshold ratio, the peak sound energy occurrence ratio being the temporal location of the peak sound energy expressed as a fraction relative to the total duration of the sampled sound energy; and
   confirming that the candidate snore event is not an isolated snore event by determining that breaths immediately preceding and following the candidate snore event include other candidate snore events; and
   a monitoring garment operatively coupled to the processor for providing respiratory and sound data from a monitored person.

18. A program product comprising a computer readable memory operatively coupled to a processor and configured with instructions for causing the processor to perform a method for determining when a person is snoring, the method comprising:

determining a candidate snore event, which comprises:
  detecting the occurrence of a person's breath using a sensor; and
  detecting the occurrence of a sound event by measuring sound energy using a microphone, wherein the occurrence of the sound event is detected when a peak sound energy occurrence ratio is greater than a threshold ratio, the peak sound energy occurrence ratio being the temporal location of the peak sound energy expressed as a fraction relative to the total duration of the sampled sound energy; and
confirming that the candidate snore event is not an isolated snore event by determining that breaths immediately preceding and following the candidate snore event include other candidate snore events.

19. A method for determining a snore event, comprising:
detecting, using a sensor, the occurrence of a person's breath when the person's breath has a volume that is less than a breath threshold;
detecting, using a microphone, the occurrence of a sound event from sound energy sampled near a person's mouth or nose when:
  the sampled sound energy is greater than a sound event threshold and lasts longer than a sound event period; and
  a peak sound energy occurrence ratio is greater than a threshold ratio, the peak sound energy occurrence ratio being the temporal location of the peak sound energy expressed as a fraction relative to the total duration of the sampled sound energy; and
determining that the detected sound event is a candidate snore event when:
  a pitch of the sampled sound energy of the sound event is greater than a minimum sound energy pitch and less than a maximum sound energy pitch; and
  a fraction of the sampled sound energy that occurs during inspiration is greater than an inspiration threshold.

20. The method of claim 19, wherein the breath threshold is between about 1 liter to about 2 liters.

21. The method of claim 19, wherein the sampled sound energy is the mean of at least about 20 to about 40 sound energy samples that are sampled at a frequency between about 1000 Hz and about 2000 Hz.

22. The method of claim 19, wherein the sound event period is between about 40 milliseconds to about 60 milliseconds.

23. The method of claim 19, wherein the threshold ratio is at least about 10%.

24. The method of claim 19, wherein the inspiration threshold is at least about 80%.

25. The method of claim 19, wherein the relative minimum pitch is between about 10 and about 20 and the relative maximum pitch is between about 25 and about 35.

* * * * *